United States Patent
Tanaka et al.

(10) Patent No.: US 7,022,083 B2
(45) Date of Patent: Apr. 4, 2006

(54) MEASUREMENT SYSTEM FOR LIVING BODIES

(75) Inventors: Naoki Tanaka, Tokyo (JP); Atsushi Maki, Fuchu (JP); Masashi Kiguchi, Kawagoe (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 302 days.

(21) Appl. No.: 10/457,478

(22) Filed: Jun. 10, 2003

(65) Prior Publication Data

US 2004/0077960 A1 Apr. 22, 2004

(30) Foreign Application Priority Data

Oct. 22, 2002 (JP) .................................. 2002-307379

(51) Int. Cl.
*A61B 5/02* (2006.01)
*A61B 5/00* (2006.01)

(52) U.S. Cl. ................ 600/504; 600/336; 600/322; 600/481; 600/479; 600/310; 600/500

(58) Field of Classification Search ......... 600/500–504, 600/479–481, 475, 476, 473, 309, 310, 322–324, 600/544, 545
See application file for complete search history.

(56) References Cited

U.S. PATENT DOCUMENTS

| | | | | |
|---|---|---|---|---|
| 4,195,626 A | * | 4/1980 | Schweizer | 600/587 |
| 4,510,944 A | * | 4/1985 | Porges | 600/500 |
| 5,203,342 A | * | 4/1993 | Sakai | 600/504 |
| 5,694,939 A | | 12/1997 | Cowings | |
| 5,779,631 A | * | 7/1998 | Chance | 600/328 |
| 5,853,370 A | * | 12/1998 | Chance et al. | 600/473 |
| 5,947,908 A | * | 9/1999 | Morris | 600/484 |
| 5,963,658 A | | 10/1999 | Klibanov et al. | |
| 6,081,743 A | * | 6/2000 | Carter et al. | 600/544 |
| 6,224,549 B1 | * | 5/2001 | Drongelen | 600/300 |
| 6,228,038 B1 | * | 5/2001 | Claessens | 600/558 |
| 6,282,438 B1 | | 8/2001 | Maki et al. | |
| 6,577,886 B1 | * | 6/2003 | Takaoka et al. | 600/407 |

FOREIGN PATENT DOCUMENTS

| | | |
|---|---|---|
| WO | WO 00/44580 | 12/1999 |
| WO | WO 02/065901 A2 | 12/2001 |
| WO | WO 02/087438 A2 | 4/2002 |

OTHER PUBLICATIONS

Atsushi Maki, Yuichi Yamashita, Yoshitoshi Ito, Eiju Watanabe, Yoshiaki Mayanagi and Hideaki Koizumi, "Spatial and Temporal Analysis of Human Motor Activity Using Noninvasive NIR Topography", Medical Physics, vol. 22, No. 12, Dec. 1995, pp. 1997–2005.

* cited by examiner

*Primary Examiner*—Robert L. Nasser
*Assistant Examiner*—Navin Natnithithadha
(74) *Attorney, Agent, or Firm*—Reed Smith LLP; Stanley P. Fisher, Esq.; Juan Carlos A. Marquez, Esq.

(57) ABSTRACT

A satisfactory averaged signal can be obtained with only a small number of repetitions of measurement in the measurement of responses to a stimulus given to a living body. A low-frequency biological fluctuation is extracted and a stimulus is presented to the living body in synchronism with the phase of the extracted fluctuation.

10 Claims, 10 Drawing Sheets

MEASUREMENT SYSTEM FOR LIVING BODIES

BACKGROUND OF THE INVENTION

1. Technical Field

The present invention relates to a measurement system for living bodies for measuring a response from a living body to a stimulus or instruction in order to obtain information about the living body.

2. Background Art

In a system for measuring a response from a living body to a given stimulus, the quality of a measurement signal can be expressed by an amplitude ratio of a response signal to other fluctuation components. The greater the amplitude ratio is, the higher the quality of the signal is. The fluctuation components are mainly fluctuations inherent in the living body (biological fluctuation components) and a noise inherent in the system. In order to improve the signal quality, according to a prior art technique, a stimulus (including a task instruction) is given repeatedly in a periodical or random manner, and the resultant response signal is calculated to obtain an arithmetic mean, as disclosed in an article A. Maki et al., Medical Physics 22, 1997–2005 (1995).

This conventional technique of giving a stimulus or instruction repeatedly in a periodical or random manner and then obtaining an arithmetic mean of the resultant signal is based on the assumption that the number of repetition is large. The random fluctuation components that appear in the arithmetic mean signal decrease in inverse proportion to the square root of the number of repetitions. However, the number of repetitions should be minimized, given the physical burden such repetitions place on the subject. Particularly, when the subject is an infant or a patient of certain diseases, it is impossible to repeat the measurement many times.

SUMMARY OF THE INVENTION

It is an object of the invention to provide a measurement system for living bodies that can ensure sufficient signal quality with a small number of measurements.

This object is achieved by extracting a biological fluctuation and presenting a stimulus in synchronism with the phase of the extracted biological fluctuation. The biological fluctuation refers to the noise contained in the measurement signal from which the system-derived noise components have been removed.

In one aspect, the invention provides a measurement system for living bodies comprising:

a measurement unit for measuring the inner state of a subject body;

a signal extraction unit for extracting a biological fluctuation component contained in a signal obtained by the measurement unit;

a stimulus timing determination unit for determining the timing of presentation of a stimulus or instruction to the subject body on the basis of the biological fluctuation component extracted by the signal extraction unit;

a stimulus/instruction presentation control unit for controlling the presentation of a stimulus or instruction such that the presentation occurs at the time determined by the stimulus timing determination unit; and a stimulus/instruction presentation unit for presenting a stimulus or instruction to the subject body in accordance with a control signal from the stimulus/instruction presentation control unit.

The biological fluctuation component extracted by the signal extraction unit may be a low-frequency component of the signal measured by the measurement unit, particularly between 0.01 and 0.5 Hz.

The signal extraction unit may output a current value of the biological fluctuation component. The current value is the value at the current time of the signal measured by the measurement unit that has been subjected to fitting with a polynomial of degree n in a time window length T (seconds) that is set from the present to the past (n=an integer of 3 or more, and n and T satisfy $0.01 \leq (n-1)/2T \leq 0.5$).

The stimulus timing determination unit may present a stimulus or instruction to the subject body based on the phase of the biological fluctuation component extracted by the signal extraction unit. For example, a stimulus or instruction can be presented alternately at the maxima and minima of the biological fluctuation component wave. Alternatively, a stimulus or instruction may be presented to the subject body at the maxima and minima of the biological fluctuation component wave such that the number of presentation of stimulus or instruction at the maxima of the biological fluctuation component wave equals the number of presentation of stimulus or instruction at the minima.

The measurement unit may include a light-irradiation unit for irradiating near infrared light to the head skin of the subject body, and a light-detection unit for detecting the intensity of light that has passed through the subject body. The measurement unit can measure blood flow conditions in the brain, for example.

DESCRIPTION OF THE INVENTION

The invention will be described by way of embodiments with reference made to the drawings.

Figure 1:
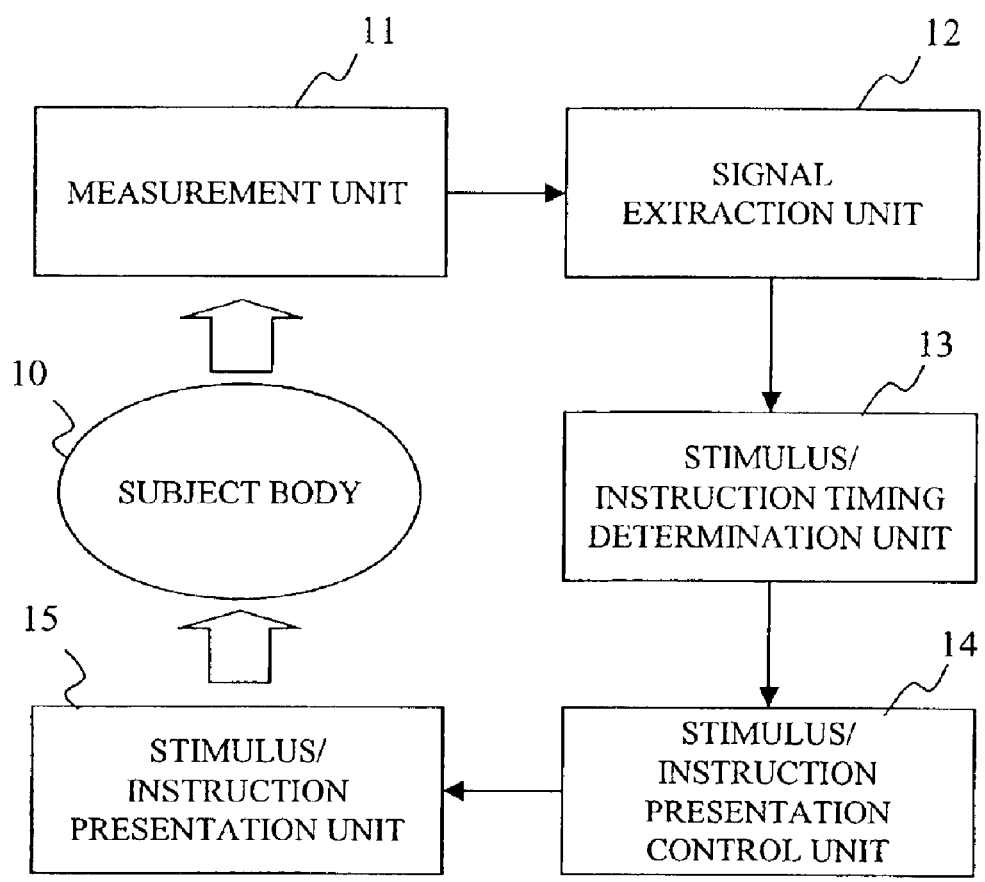
FIG. 1 shows a block diagram of an example of the measurement system for living bodies according to the invention.

FIG. 1 shows a block diagram of a measurement system for living bodies according an embodiment of the invention. As shown, the system includes a measurement unit 11, a signal extraction unit 12, a stimulus/instruction timing determination unit 13, a stimulus/instruction presentation control unit 14, and a stimulus/instruction presentation unit 15. The measurement unit 11 measures the internal state of a subject body 10. The signal extraction unit 12 extracts a certain frequency band component (biological fluctuation component) of a signal obtained by the measurement unit 11. The stimulus/instruction timing determination unit 13 determines the timing of presentation of a stimulus or instruction to the subject body 10, based on the signal component extracted by the signal extraction unit 12. The stimulus/instruction presentation control unit 14 controls the presentation of a stimulus or instruction such that it is presented at the time determined by the stimulus/instruction timing determination unit 13. The stimulus/instruction presentation unit 15 presents a stimulus or instruction to the subject body 10 in accordance with a control signal from the stimulus/instruction presentation control unit 14.

A stimulus herein refers to that which requires a passive action (such as listening to a sound or seeing a figure) on the part of the subject body. An instruction herein refers to that which requires an active action (such as listening to a sound or seeing a figure and then pushing a button) from the subject body. Measurement can be taken in a variety of terms. Examples include electroencephalogram (EEG), blood flow, oxy hemoglobin or deoxy hemoglobin concentration in the blood, total hemoglobin concentration, local magnetic field in the brain, blood radioactive species concentration, proton relaxation time, myogenic potential, and skin potential. The means of measurement include, for example, electroencephalographs, ammeters, optical measurement devices, magnetic resonance apparatus, magnetoencephalographs, PET (positron emission tomography), fMRI (functional magnetic resonance imaging), myogenic potential meters, and skin potential meters (electrocardiographs).

Figure 2:
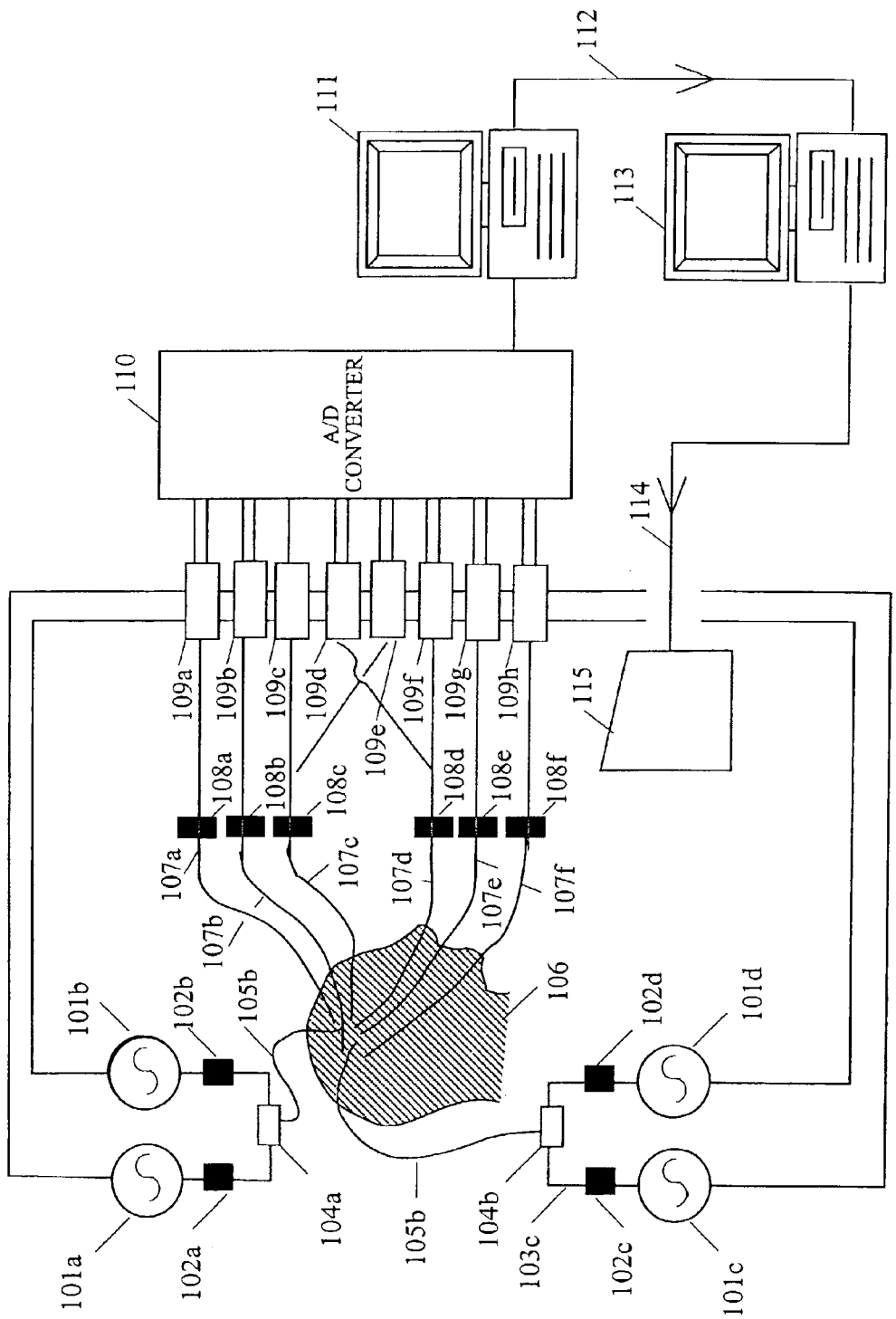
FIG. 2 shows an example of the measurement system for living bodies as applied to the optical measurement of brain activities.

In the following, an example will be considered in which the invention is applied to the optical measurement of brain activities in a newborn baby. FIG. 2 shows the measurement system.

Light sources 102a and 102c emit near infrared light with a wavelength of 780 nm. Light sources 102b and 102d emit near infrared light with a wavelength of 830 nm. The light sources 102a and 102c, and 102b and 102d, are driven with different frequencies by oscillators 101a to 101d. The lights from the light sources 102a and 102b that are intensity-modulated with different frequencies travel through optical fibers 103a and 103b, respectively, and are combined in a coupler 104a. The combined light is passed through a light-irradiation optical fiber 105a and irradiated onto a point on the scalp of a subject 106 that is the subject body. The lights from the other light sources 102c and 102d travel through optical fibers 103c and 103d to a coupler 104b where they are combined. The combined light is then passed through a light-irradiation optical fiber 105b and irradiated onto another point on the scalp of the subject 106.

Near where light is irradiated via the light-irradiation optical fibers 105a and 105b is disposed a plurality of light-receiving optical fibers 107a to 107f such that their tips are located an equal distance (30 mm in the example) away from each irradiated position. The rear end of each of the light-reception optical fibers is provided with a photodetector 108a to 108f such as, for example, a photomultiplier or a photodiode. Light that has passed through the living body ("living-body transmitted light") is received by the six light-receiving optical fibers 107a to 107f. The thus received living-body transmitted light is individually converted into an electric signal by the photodetectors 108a to 108f. The term "living-body transmitted light" refers to light that has passed through the living body and then received by the light-receiving fibers 107a to 107f, including both reflected light and transmitted light.

The electric signal ("living-body transmitted light intensity signal") produced by each of the photodetectors 108a to 108f indicates the intensity of light that has passed through the living body. The individual signals are fed to lock-in amplifiers 109a to 109h. The living-body transmitted light whose intensities are detected by the photodetectors 108c and 108d is collected by the light-reception optical fibers 107c and 107d that are located an equal distance from both the light-irradiating optical fibers 105a and 105b. Accordingly, the signal from the photodetector 108c and 108d each is divided into two lines, one connecting to the lock-in amplifiers 109c and 109e, the other connecting to the lock-in amplifiers 109d and 109f. The intensity modulation frequencies from the oscillators 101a and 101b are supplied to the lock-in amplifiers 109a to 109d. The intensity modulation frequencies from the oscillators 101c and 101d are supplied to the lock-in amplifiers 109e to 109h. The frequencies are used as reference frequencies. Thus, the lock-in amplifiers 109a to 109d separate and output a living-body transmitted light intensity signal corresponding to the light sources 102a and 102b. The lock-in amplifiers 109e to 109h separate and output a living-body transmitted light intensity signal corresponding to the light sources 102c and 102d.

The thus separated living-body transmitted light intensity signals of the individual wavelengths produced by the lock-in amplifiers 109e to 109h are analog-digital converted by an analog/digital converter 110 and then sent to a measurement control computer 111. The measurement control computer 111 processes the living-body transmitted light intensity signals according to the procedure as described in the above-mentioned Non-Patent Document 1, for example, and calculates, from the detection signal at each detection point, relative amounts of change of oxy hemoglobin concentration, deoxy hemoglobin concentration, and total hemoglobin concentration. The computer 111 then stores the obtained values in a storage unit as chronological information concerning the multiple measurement points, while sending a measurement signal 112 of a pre-selected channel to a filtering-calculation computer 113. The amount of change of the total hemoglobin concentration is the sum of the amounts of change of oxy and deoxy hemoglobin. The term "channel" refers to a combination of the measurement position and the measurement species (either oxy, de-oxy, or total hemoglobin). The filtering-calculation computer 113 extracts a fluctuation component of a specific frequency band by filtering using polynomial fitting, as will be described below. The filtering-calculation computer 113 then sends a control signal 114 to a stimulation/instruction presentation unit 115 so that a stimulus or instruction is presented at the maxima and minima of the fluctuating wave.

Figure 3:
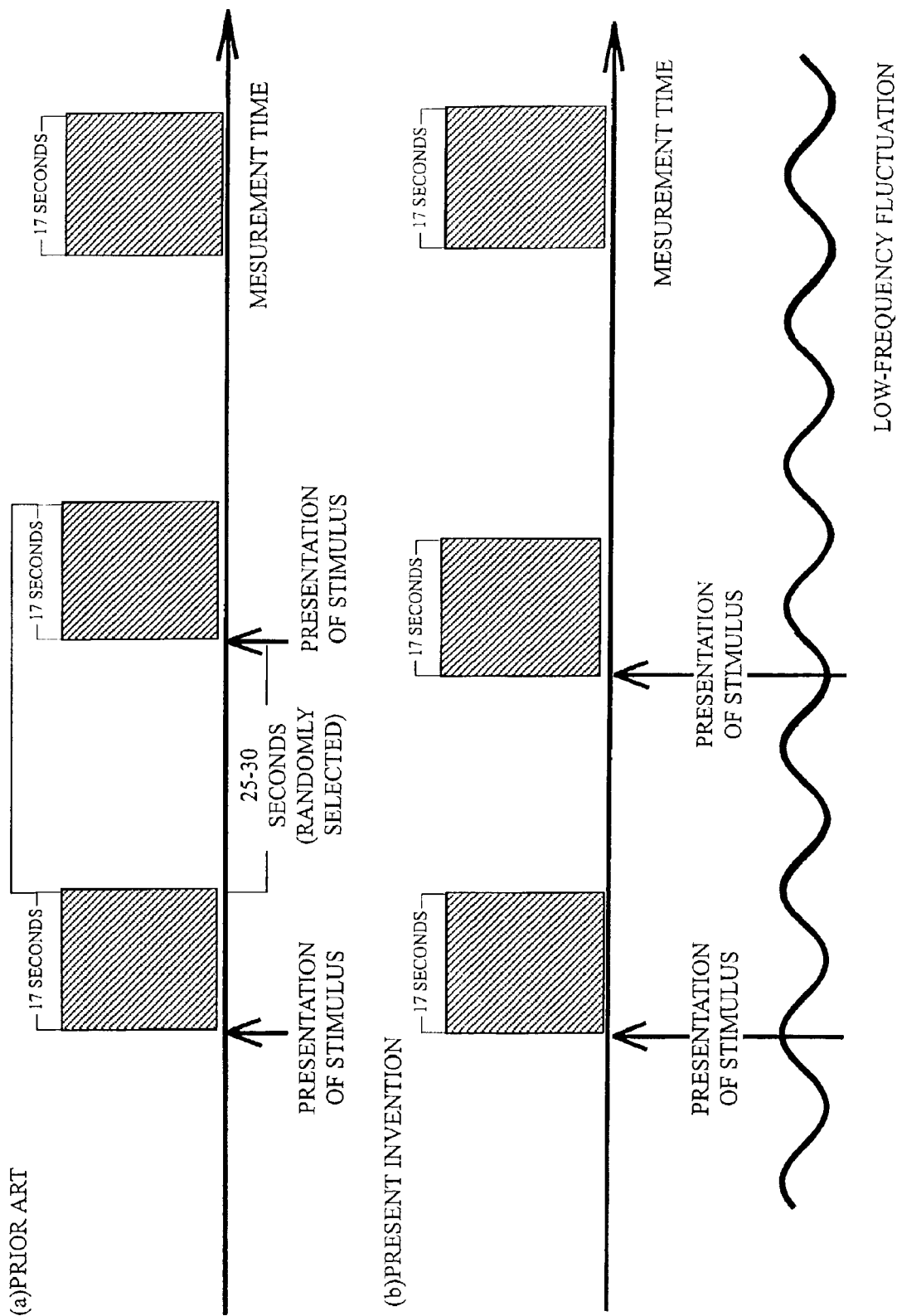
FIG. 3 illustrates the timing of presentation of a stimulus or instruction.

FIG. 3 shows an example of the stimulation timing in the present embodiment in comparison with the timing in a conventional system. The rectangular waveforms indicate the time at which a stimulation was given. The stimulation consisted of an auditory stimulation lasting for 17 seconds. In the conventional system, the rest period between one presentation of stimulation and the next is randomly selected between 25 to 35 seconds. In the present embodiment, on the other hand, the stimulation is presented at the maxima and minima of a low-frequency fluctuation wave.

The low-frequency fluctuation is extracted by the filtering-calculation computer 113. Major biological fluctuations are distributed near 0.1 Hz in infants as well as in adults (H. Obrig et al., NeuroImage 12, 623–639 (2000)). When such low-frequency fluctuations are extracted by the normal filtering technique in a frequency range, the influence of delay cannot be ignored. Such a disadvantage is overcome in the present embodiment by filtering based on polynomial fitting in a preset time window.

Figure 4:
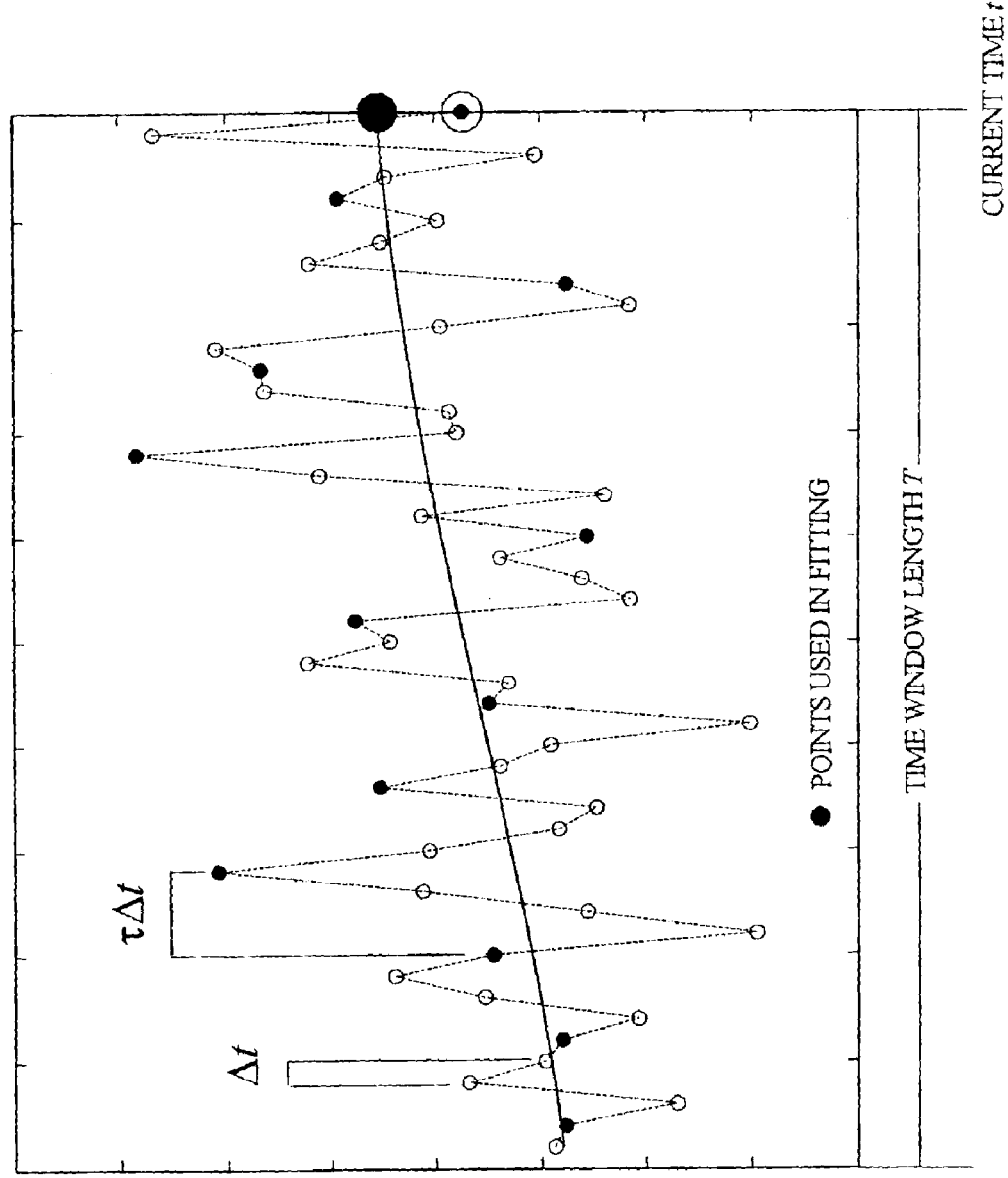
FIG. 4 shows a chart for the description of polynomial fitting.

Referring to FIG. 4, the polynomial fitting technique will be described. In the figure, $\Delta t$ is a sampling interval, which is 0.1 second in the present embodiment. $T\Delta t$ is the interval of data used in fitting, which is 0.1 second in the present embodiment, meaning that all of the sampling points are used. T is the length of a time window, which is 15 seconds in the present embodiment. The number of terms in the polynomial is 3. Increasing the order of the polynomial produces the same effect as shortening the time window length T on filtering. As the order of the polynomial is raised, or the time window length T is shortened, the extracted biological fluctuations shift to higher frequencies.

A typical frequency of the extracted signal components is given by (Order of polynomial-1)/2T (Hz). The typical frequency should desirably be somewhere between 0.01 to 0.5 Hz in light of the object of the invention. This is because 1) the frequency components of the stimulus response signal is 1 Hz at most; 2) the stimulus (task) period is typically on the order of several tens of seconds; and 3) important low-frequency fluctuations exist in this range, as described in the above-mentioned publication (H. Obrig et al., NeuroImage 12, 623–639 (2000)). In the example of FIG. 4, filtering is carried out on a measurement signal at time t. Against measurement data x(s) in the time window length T, the following polynomial of degree 3 is applied:

$$x(s)=as^3+bs^2+cs+d$$

wherein $t-T \leq s \leq t$.

The coefficients are determined by a least square method. Supposing their estimated values are $<a>$, $<b>$, $<c>$, and $<d>$, the estimated values of a smoothed signal, a first-order derivative, and a second-order derivative at the current time t are expressed as follows:

$$<x(t)>=<a>t^3+<b>t^2+<c>t+<d>$$

$$<dx(t)/dt>=3<a>t^2+2<b>t+<c>$$

$$<d^2x(t)/dt^2>=6<a>t+2<b>$$

In FIG. 4, the large hollow circle at current time t indicates a measured signal value, while the large solid circle indicates a smoothed signal value. The smoothed signal value is an estimated value at current time t of the extracted low-frequency fluctuation. The small solid circles indicate data used in fitting, while small hollow circles indicate data that is not used in fitting.

Figure 5:
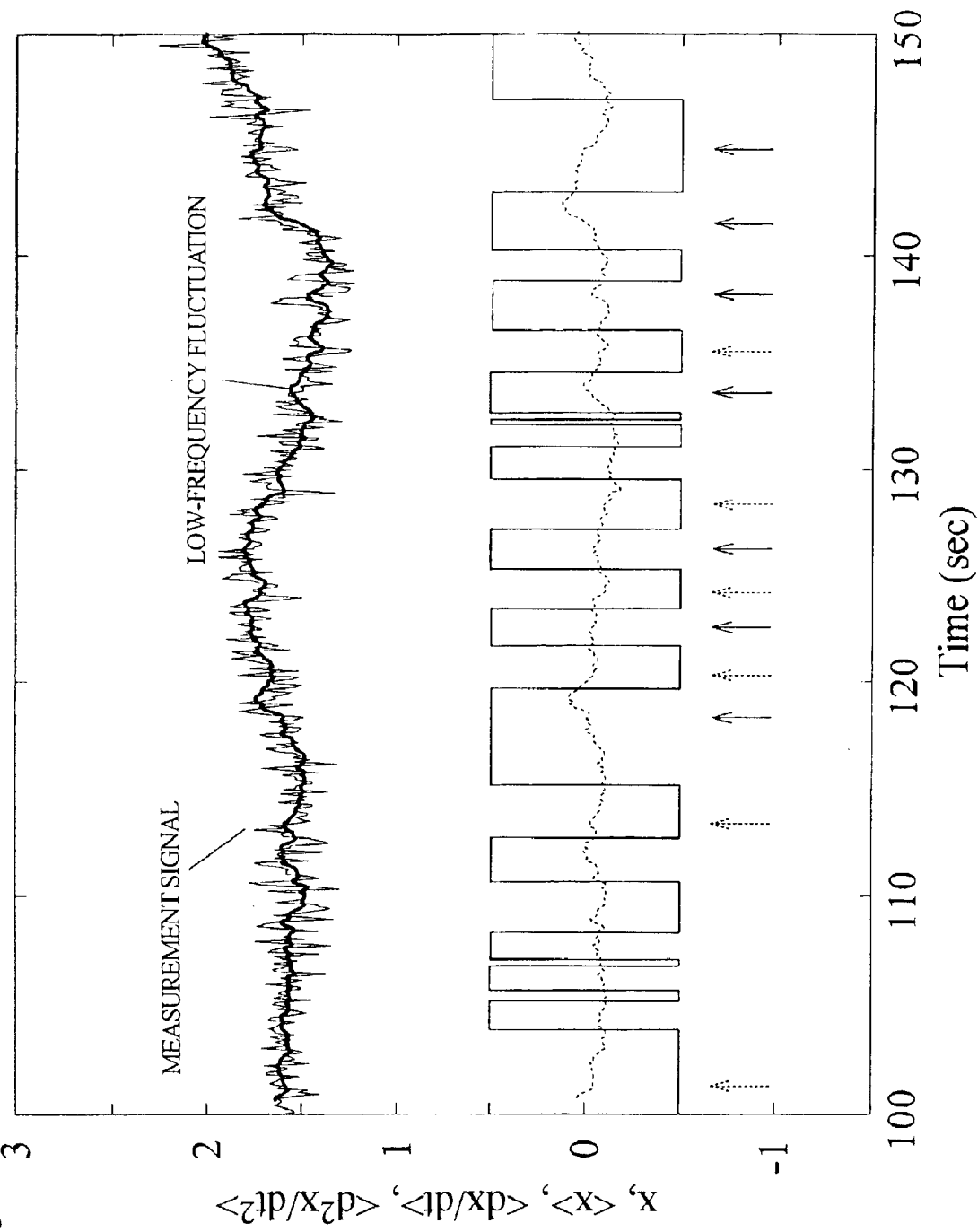
FIG. 5 shows a chart indicating the positions of maxima and minima of a low-frequency fluctuation wave that were detected by polynomial fitting.

FIG. 5 shows an example where a low-frequency fluctuation was extracted from a newborn baby under no stimulus environment and where the positions of the maxima and minima of the low-frequency fluctuation were detected. At the top of the figure, the thin solid line indicates a measurement signal and the thick solid line indicates the smoothed signal, namely the extracted low-frequency fluctuation. At the bottom, the broken line indicates the first-order derivative, and the rectangle waveform indicates the second-order derivative. The solid arrows indicate the positions of the maxima of the detected fluctuating wave, while the broken arrows indicate the positions of its minima.

Figure 6:
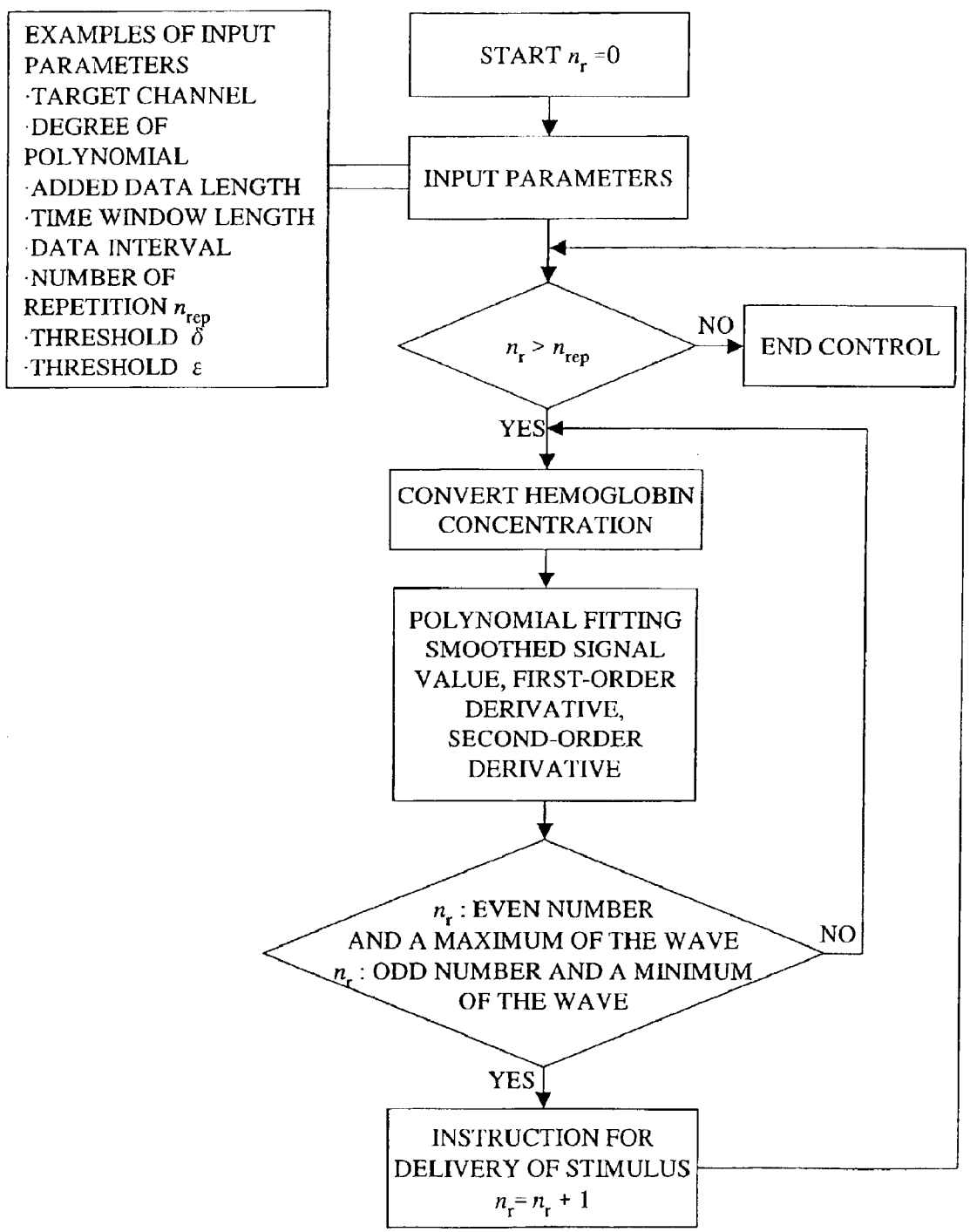
FIG. 6 shows an algorithm for the control of a stimulus/instruction presentation unit.

Referring to FIG. 6, a control algorithm for the stimulus/instruction presentation unit used in this example will be described. First, various parameters are input, including a target channel, degree of the polynomial, length of added data (the length of a stimulus response), time window length, interval of data used in polynomial fitting, number of repetition $n_{rep}$ (number of presentation of stimulus or instruction), and two kinds of thresholds $\delta$, $\epsilon(>0)$. The number of actual presentation of a stimulus or instruction is $n_r$, and the control comes to an end when $n_r=n_{rep}$. Based on the measurement signal, a polynomial fitting is carried out, and the low-frequency fluctuation (biological fluctuation), its first-order derivative and a second-order derivative are estimated. A control signal 114 for the presentation of a stimulus/instruction is sent to the stimulus/instruction presentation unit 115 when $n_r$ is an even number (including 0) and at the timing of a maximum of the fluctuation wave, or when $n_r$ is an odd number and at the timing of a minimum of the fluctuation wave. $n_r$ is incremented such that $n_r=n_r+1$ and the control is continued and this is repeated until $n_r=n_{rep}$.

The positions of maxima and minima of the fluctuation wave as the measurement signal was consecutively sent from the measurement control computer 111 were determined using the following algorithm. That is, a maximum was recognized when the absolute value of the first-order derivative was smaller than the threshold $\delta$ and the second-order derivative was smaller than $-\epsilon$. A minimum was recognized when the absolute value of the first-order derivative was smaller than the threshold $\delta$ and the second-order derivative was larger than $\epsilon$. In the present embodiment, the thresholds were $\delta=0.05$ and $\epsilon=0.005$. While the maxima and minima were selected alternately, this is not a requirement, and the same effect can be obtained by assigning half of the number of repetition to the maxima and the remaining half to the minima. The base line tends to project upward at the maxima and downward at the minima. By adding the same number of maxima and minima together, they cancel each other out and as a result, a flat base line can be obtained.

Figure 7:
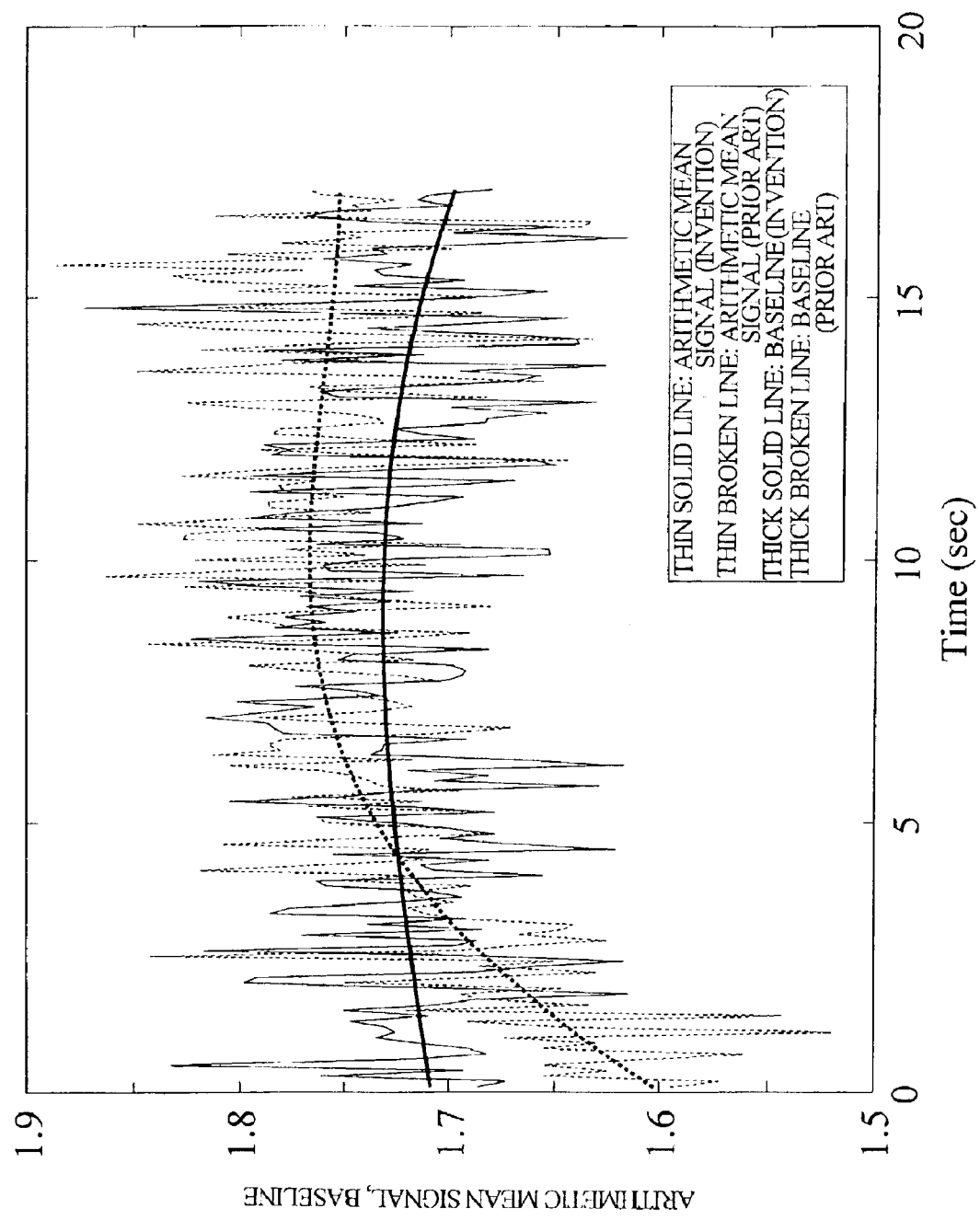
FIG. 7 shows a chart indicating arithmetic mean signals and their baselines.

In the present embodiment, the relative changes of oxy hemoglobin concentration and deoxy hemoglobin concentration at six sites (indicated by numerals 1 to 6) on the left and right temporal regions are measured. These amounts of change are calculated with reference to the living-body transmitted light intensity 10 seconds after start of measurement. FIG. 7 shows the results of selecting the oxy hemoglobin concentration change at measurement site 1 as the measurement signal 112 and repeating the presentation of stimulus 10 times. In this example, the effect of the invention is indicated with regard to the target channel. The effect is evaluated based on the standard deviation of baseline variation, which should preferably be flat. It can be seen that the stimulus-presentation method according to the invention as shown in FIG. 3(b) is capable of reducing the standard deviation of baseline variation better than the conventional stimulus-presentation method indicated in FIG. 3(a).

Figure 8:
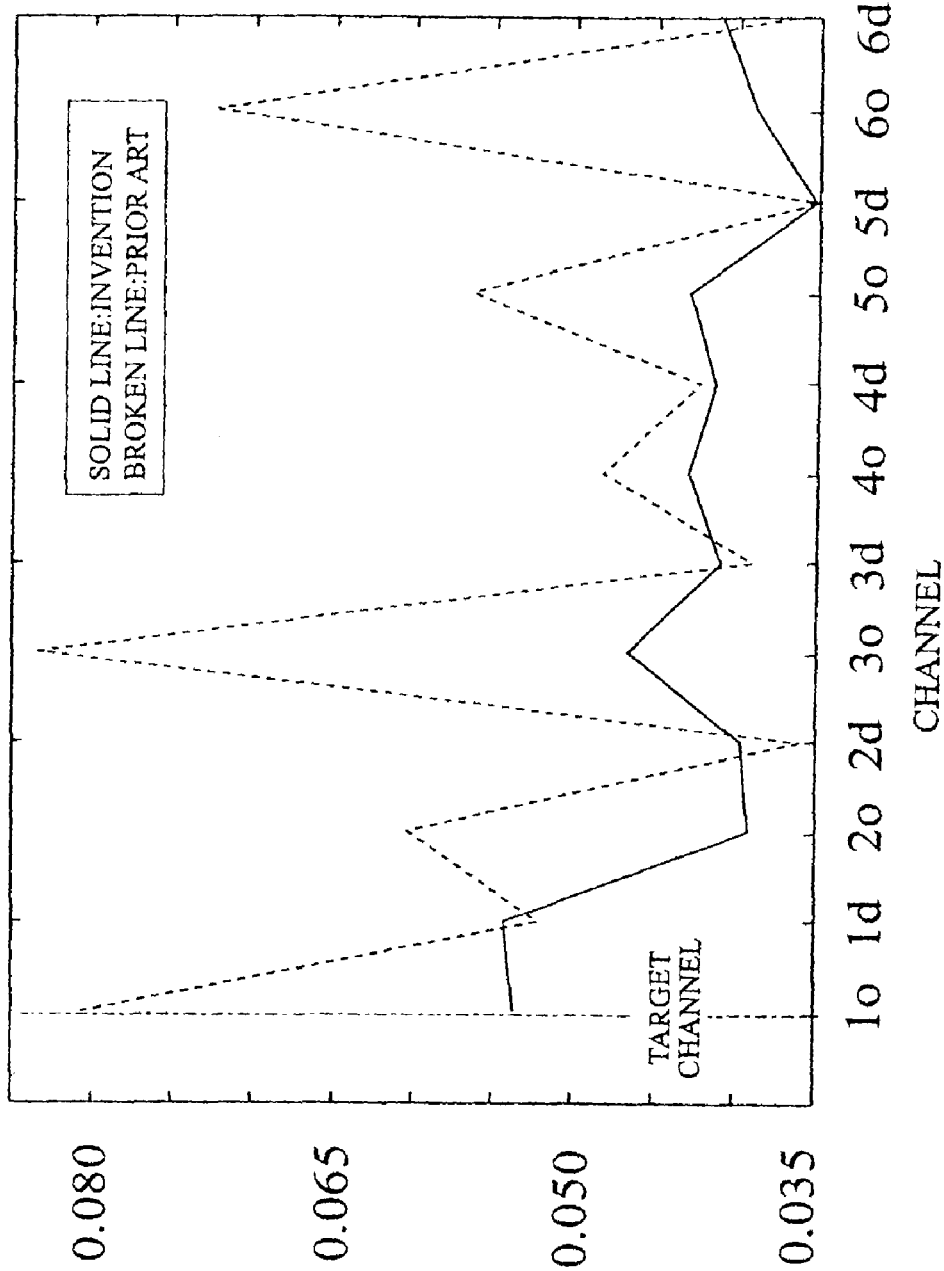
FIG. 8 shows a chart indicating the standard deviation of the arithmetic mean signal baseline in each channel when a channel corresponding to an oxy hemoglobin concentration change at measurement site 1 was selected as the target channel.

FIG. 8 shows the influence of the other channels on the baseline variation. The horizontal axis indicates the channel numbers and the vertical axis indicates the standard deviation of the baseline variation. The solid line indicates the results of the present embodiment, while the broken line indicates the results of the conventional example. With regard to the changes in oxy hemoglobin concentration at other measurement sites, the baseline variation is sufficiently suppressed in the present embodiment as compared with the conventional example, as will be seen from the comparison of the two values at channels 2o, 3o, 4o, 5o, and 6o. Regarding the deoxy hemoglobin concentration, the invention can also provide results comparable to those of the conventional example.

Figure 9:
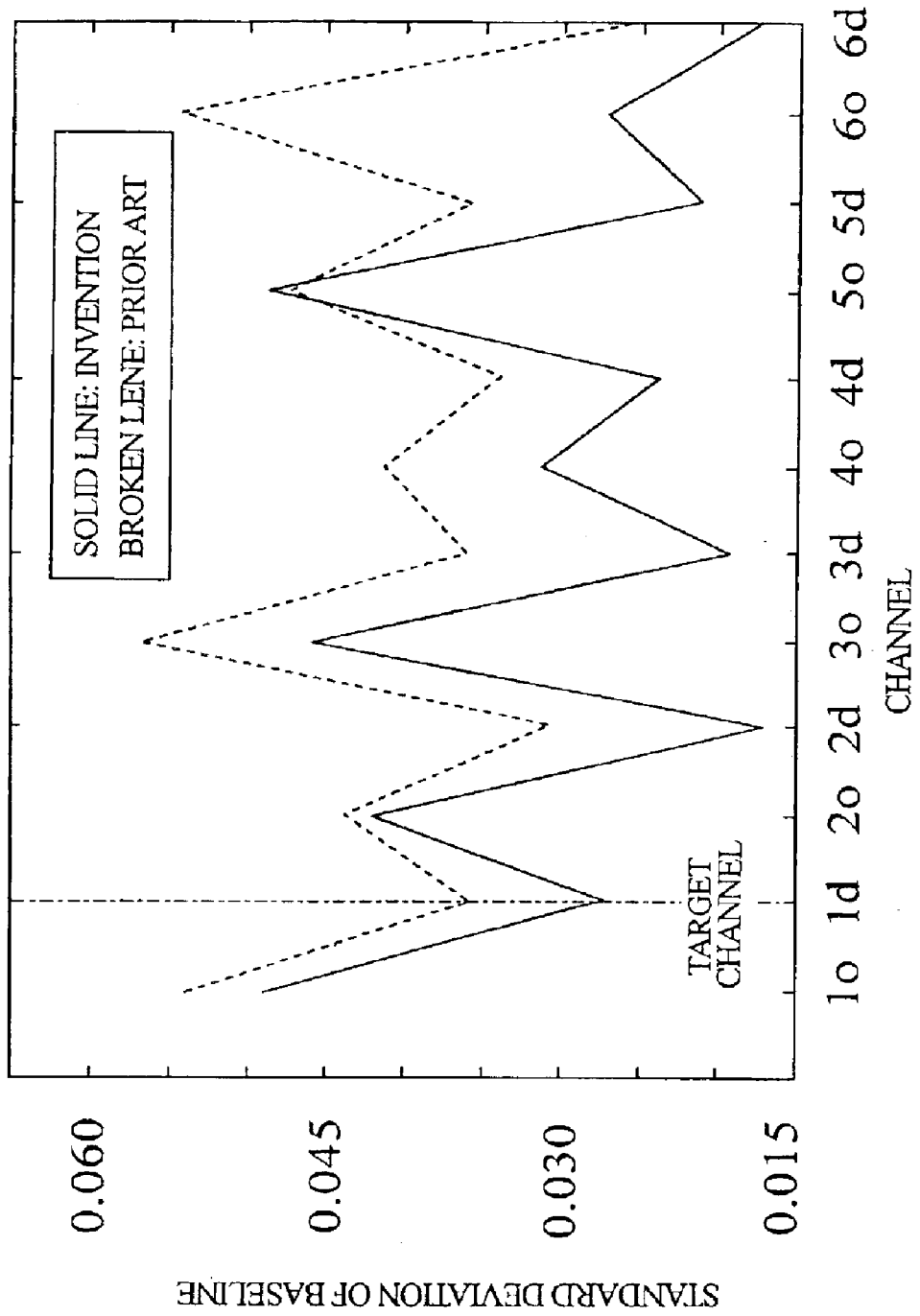
FIG. 9 shows a chart indicating the standard deviation of the arithmetic mean signal baseline in each channel when a channel corresponding to a deoxy hemoglobin concentration change at measurement site 1 was selected as the target channel.

These tendencies did not change when other channels were selected as the target. For example, when 1d was selected as the target channel, sufficient effects were obtained for the deoxy hemoglobin concentration change at other measurement sites in addition to sufficient effects at the target channel 1d, as shown in FIG. 9. Regarding the oxy hemoglobin concentration change, results tended to be comparable to those obtained by the conventional example. When the total hemoglobin concentration change is selected as the target channel, the effects consisted of an average of the above-mentioned two tendencies. It is also possible to select a plurality of target channel candidates in advance and then change the target channel in a certain order, or to select a plurality of channels from all of the channels and then monitor their average value which is then used in controlling the stimulus/instruction presentation timing.

Figure 10:
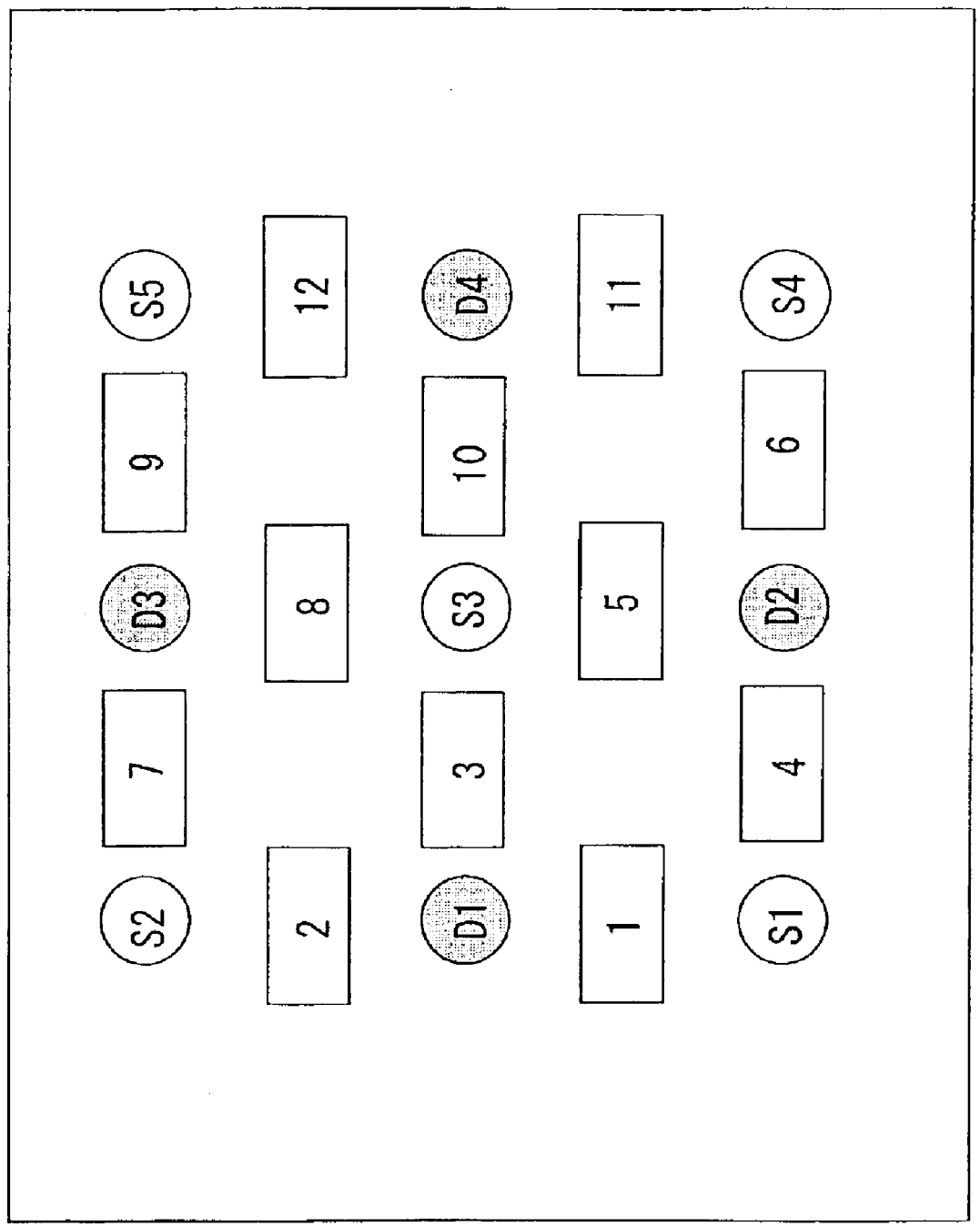
FIG. 10 shows an arrangement of light irradiation and light-reception optical fibers.

In a next experiment, optical fibers were disposed on the left temporal region of the head of an adult subject, as shown in FIG. 10, and the language-related function of the brain was optically measured by the system according to the invention. In the figure, S indicates the position of light-source fibers, while D indicates the position of light-receiving fibers. The numerals enclosed by rectangles between Ss and Ds indicate the measurement positions.

The distance between the adjacent Ss and Ds was 30 mm, and the wavelengths of the light source used were 781 nm and 832 nm. As described with reference to the above-described embodiments, the relative concentration changes of oxy hemoglobin, deoxy hemoglobin, and total hemoglobin at measured sites can be known by optical measurement. The fibers were arranged as shown in FIG. 10 such that the language-related sites that have been identified by fMRI (functional magnetic resonance imaging), for example, were covered. While the subject was performing a language task, a significant increase in the amount of oxy hemoglobin was observed at a measurement site 3. Thus, the channel corresponding to the oxy hemoglobin at the measurement site 3 was selected as the target channel.

The language task assigned to the subject was a word-chain game (in which the subject had to come up with a word that begins with the same sound as that of the last syllable of the previous word), and it lasted for 40 seconds. This was followed by a rest of 40 seconds, during which the subject had to repeat the sounds of "ah," "ii," "oo," "eh," "oh." This sequence was repeated five times using the conventional system and the system of the invention, and the S/N amplitude ratios of arithmetic mean response signals that were obtained for the target channel were compared. The filtering conditions included a time window length of 20 seconds and the degree of 5 of the polynomial. The thresholds were the same as those in the above-described embodiments. As a result, the S/N amplitude ratio was 1.2 for the conventional system against 2.5 for the system of the invention, thus illustrating the advantageous effect of the invention.

Thus, in accordance with the invention, a high level of signal quality can be ensured in measuring responses to a stimulus given to a living body. Particularly, when the measurement is repeated a small number of times, a better signal quality can be obtained than in the case of periodical or random presentation of stimulus.

What is claimed is:

1. A measurement system for living bodies, comprising:
   a measurement unit for measuring the internal state of a subject body;
   means for detecting the position of a maximum and a minimum of a biological fluctuation component;
   a signal extraction unit for extracting the biological fluctuation component contained in a signal obtained by the measurement unit, wherein the signal extraction unit outputs a current value of the biological fluctuation component which is the value of the signal measured by the measurement unit at the current time when the signal has been subjected to fitting with a polynomial of degree n in a time window length T, seconds, that is set from the present to the past, n=an integer of 3 or more, $0.01 \leq (n-1)/2T \leq 0.5$;
   a stimulus timing determination unit for determining the timing of presentation of a stimulus or instruction to the subject body on the basis of the biological fluctuation component extracted by the signal extraction unit, wherein the stimulus timing determination unit determines the timing of presentation of a stimulus or instruction to the subject body alternately at the maxima and minima of the biological fluctuation component extracted by the signal extraction unit;
   a stimulus/instruction presentation control unit for controlling the presentation of a stimulus or instruction such that the presentation occurs at the time determined by the stimulus timing determination unit; and
   a stimulus/instruction presentation unit for presenting a stimulus or instruction to the subject body in accordance with a control signal from the stimulus/instruction presentation control unit.

2. The measurement system for living bodies according to claim 1, wherein the signal extraction unit extracts a low-frequency component of the signal measured by the measurement unit.

3. The measurement system for living bodies according to claim 2, wherein the low-frequency component is in the range between 0.01 Hz to 0.5 Hz.

4. The measurement system for living bodies according to claim 1, wherein the stimulus timing determination unit determines the timing of presentation of a stimulus or instruction to the subject body on the basis of the phase of the biological fluctuation component extracted by the signal extraction unit.

5. The measurement system for living bodies according to claim 1, wherein the measurement unit comprises:
   a light irradiation unit for irradiating near infrared light to the head skin of the subject body; and
   a light detection unit for detecting the intensity of living-body transmitted light that has been transmitted through the subject body.

6. A measurement system for living bodies, comprising:
   a measurement unit for measuring the internal state of a subject body;
   means for detecting the position of a maximum and a minimum of a biological fluctuation component;
   a signal extraction unit for extracting the biological fluctuation component contained in a signal obtained by the measurement unit, wherein the signal extraction unit outputs a current value of the biological fluctuation component which is the value of the signal measured by the measurement unit at the current time when the signal has been subjected to fitting with a polynomial of degree n in a time window length T, seconds, that is set from the present to the past, n=an integer of 3 or more, $0.01 \leq (n-1)/2T \leq 0.5$;

a stimulus timing determination unit for determining the timing of presentation of a stimulus or instruction to the subject body on the basis of the biological fluctuation component extracted by the signal extraction unit, wherein the stimulus timing determination unit determines the timing of presentation of a stimulus or instruction to the subject body at the maxima and minima of the biological fluctuation component extracted by the signal extraction unit such that the number of presentation of the stimulus or instruction at the maxima equals the number of presentation of the stimulus or instruction at the minima;

a stimulus/instruction presentation control unit for controlling the presentation of a stimulus or instruction such that the presentation occurs at the time determined by the stimulus timing determination unit; and a stimulus/instruction presentation unit for presenting a stimulus or instruction to the subject body in accordance with a control signal from the stimulus/instruction presentation control unit.

7. The measurement system for living bodies according to claim 6, wherein the measurement unit comprises:

a light irradiation unit for irradiating near infrared light to the head skin of the subject body; and a light detection unit for detecting the intensity of living-body transmitted light that has been transmitted through the subject body.

8. The measurement system for living bodies according to claim 6, wherein the signal extraction unit extracts a low-frequency component of the signal measured by the measurement unit.

9. The measurement system for living bodies according to claim 8, wherein the low-frequency component is in the range between 0.01 Hz to 0.5 Hz.

10. The measurement system for living bodies according claim 6, wherein the stimulus timing determination unit determines the timing of presentation of a stimulus or instruction to the subject body on the basis of the phase of the biological fluctuation component extracted by the signal extraction unit.

* * * * *